United States Patent [19]

Merry et al.

[11] 4,080,963
[45] Mar. 28, 1978

[54] FENESTRATED DRAPE

[75] Inventors: Jack D. Merry, Sleepy Hollow; Mark W. Kolstedt, Cary, both of Ill.

[73] Assignee: The Kendall Company, Boston, Mass.

[21] Appl. No.: 742,155

[22] Filed: Nov. 15, 1976

[51] Int. Cl.² .............................................. A61F 13/00
[52] U.S. Cl. ................................................ 128/132 D
[58] Field of Search ........................... 128/132 D, 292

[56] References Cited

U.S. PATENT DOCUMENTS

| 3,669,106 | 6/1972 | Schrading | 128/132 D |
|---|---|---|---|
| 3,741,206 | 6/1973 | Binard et al. | 128/132 D |
| 3,835,851 | 9/1974 | Villari | 128/132 D |

Primary Examiner—Lawrence W. Trapp
Attorney, Agent, or Firm—Powell L. Sprunger

[57] ABSTRACT

A folded drape comprising, a sheet of flexible material including a first surface for contacting the body of a patient after placement of the drape, and an opposed second surface. The sheet has first and second spaced lateral fold lines defining a central panel having a fenestration located adjacent a lateral central portion thereof, and a third lateral fold line located intermediate the central panel and one end edge of the sheet, with the third fold line defining an end panel intermediate the one end edge and the third fold line, and with the first fold line being located intermediate the second and third fold lines. The sheet has a connecting panel intermediate the first and third fold lines, with the connecting panel being folded into a configuration overlying the first surface and a first end portion of the central panel, with the third fold line being spaced from the second fold line and the first surface of a second end portion of the central panel being exposed intermediate the second and third fold lines, and with the fenestration being located in the second end portion and the first surface of the end panel being exposed in the folded configuration. The drape has a pair of first adhesive zones located on opposed sides of and adjacent the fenestration in the second end portion, with the first adhesive zones facing outwardly from the first surface. The drape has a pair of second adhesive zones on the end panel adjacent opposed side edges of the sheet, with the second adhesive zones facing outwardly from the first surface. The drape also has pairs of first and second release sheets respectively covering and releasably attached to the first and second adhesive zones.

10 Claims, 5 Drawing Figures

FENESTRATED DRAPE

BACKGROUND OF THE INVENTION

The present invention relates to fenestrated drapes, and more particularly to drapes having adhering means for securing the drape to the body of a patient.

Prior to a percutaneous procedure or surgery, the area of the patient's body surrounding the location for penetration or incision is usually sterilized or prepped. Since the area of the body outlying the prepped area is considered to be in a non-sterile condition, a sterile drape is frequently placed over the patient's body, and the penetration is performed through an opening in the drape. Such drapes may cover a substantial portion of the nonsterile body area to prevent contamination of the physician or surgeon during the operation, and confine the flow of fluid which otherwise is inconvenient for the physician and may result in the spreading of contamination. Preferably, the drapes are secured to the patient's body to prevent slippage and movement during the procedure, whether the drape is positioned horizontally or vertically on the body.

Since it is necessary to maintain sterile conditions throughout the procedure, the surface of the drape facing the physician must remain sterile to prevent contamination of the physician. Various types of drapes, which are adherable to the patient in some manner, have been proposed in a number of U.S. patents, such as, Creager, Jr. et al U.S. Pat. No. 3,364,928, Melges U.S. Pat. No. 3,503,391, Questal U.S. Pat. No. 3,260,260, Blanford, U.S. Pat. No. 3,349,765, Blanford, U.S. Pat. No. 3,452,750, Pereny et al U.S. Pat. No. 3,060,932, Orndorff, U.S. Pat. No. 3,111,943, Melges, U.S. Pat. No. 3,494,356, Morgan, U.S. Pat. No. 3,263,680, Binard, et al U.S. Pat. No. 3,741,206, and Villari, U.S. Pat. No. 3,835,851.

If the sterile drape has any considerable bulk, it is desirable to fold the drape for convenience of packaging and storage, and the drape should be folded into a configuration such that it may be unfolded without contaminating the drape. Moreover, the drape should be folded into a configuration in order that the adhesive may be readily exposed in a convenient manner, and it is desirable that the drape may be utilized on patients of varying sizes, such as adults and infants.

SUMMARY OF THE INVENTION

A principal feature of the present invention is the provision of a sterile fenestrated drape which may be placed on patients of different body sizes.

The drape of the present invention comprises a sterile sheet of flexible material. The sheet has a pair of side edges extending longitudinally along the sheet, a pair of laterally extending end edges connecting the side edges, a first surface for contacting the body of a patient after placement of the drape, and a second surface facing away from the patient after placement of the drape. The sheet has first and second spaced lateral fold lines extending between the side edges and defining a laterally extending central panel having a fenestration located adjacent a lateral central portion thereof, and a third lateral fold line extending between the side edges and located intermediate the central panel and one of the end edges, with the third fold line defining a laterally extending end panel intermediate the one end edge and the third fold line, and with the first fold line being located intermediate the second and third fold lines.

The sheet has at least one laterally extending connecting panel intermediate the first and third fold lines, with the panel being folded into a configuration overlying the first surface and a first end portion of the central panel, with the first end portion being covered between the first and third fold lines, with the third fold line being spaced from the second fold line and the first surface of a second end portion of the central panel being exposed intermediate the second and third fold lines, and with the fenestration being located in the second end portion and the first surface of the end panel being exposed in the folded configuration. The sheet has at least one end section extending from the second fold line and folded beneath the central panel. The drape has a pair of first adhesive zones located on opposed sides of and adjacent the fenestration in the second end portion of the central panel, with the first adhesive zones facing outwardly from the first surface. The drape has a pair of first release sheets covering and releasably attached to the first adhesive zones. The drape has a pair of second adhesive zones on the end panel adjacent opposed side edges of the sheet, with the second adhesive zones facing outwardly from the first surface. The drape also has a pair of second release sheets covering and releasably attached to the second adhesive zones.

A feature of the present invention is that the release sheets are exposed and may be readily removed from the adhesive zones without contamination to the drape.

Another feature of the invention is that the release sheets may include end portions extending past respective fold lines in order to facilitate removal of the release sheets from the adhesive.

Still another feature of the invention is that the first and second adhesive zones may be selectively exposed for use in connection with patients of different sizes.

Thus, a feature of the invention is that the first adhesive zones may be exposed for attachment against an infant while the remaining portion of the drape may be folded over the infant.

Yet another feature of the invention is that both the first and second adhesive zones may be exposed for securing the drape in place on an adult having a larger body size.

Another feature of the invention is that the drape may be secured to the patient in a simplified manner.

Further features will become more fully apparent in the following description of the embodiments of this invention and from the appended claims.

DESCRIPTION OF THE PREFERRED EMBODIMENTS

Figure 1:
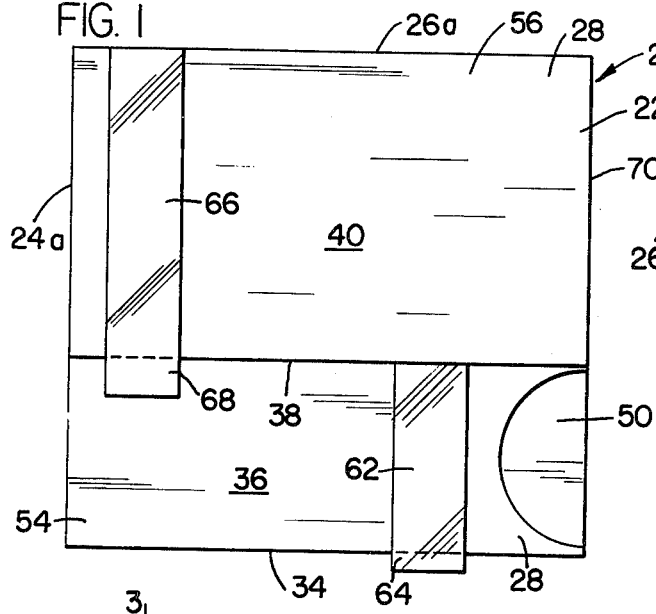
FIG. 1 is a plan view of a folded drape of the present invention.
Figure 5:
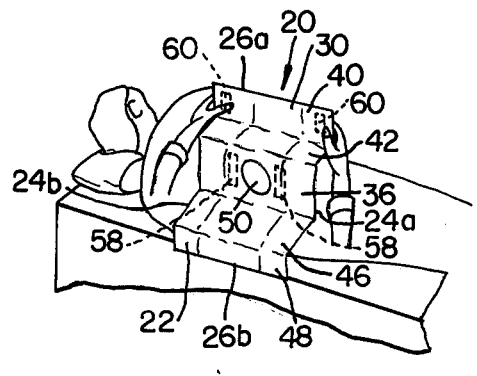
FIG. 5 is a perspective view illustrating placement of the drape on a patient.

Referring now to the drawings, a fenestrated drape, generally designated 20, is shown in a folded and unfolded configuration in FIGS. 1 and 5, respectively. The drape 20 comprises a sterile flexible sheet designated generally 22 which may be constructed from any suitable material, such as Dexter material — X1433K made by C. H. Dexter, a division of Dexter Corp., and may include a liquid impervious material to prevent passage of fluid through the sheet during percutaneous procedures or surgery. Examples of procedures for which the drape 20 may be conveniently utilized include, myelography, lumbar puncture, spinal anesthesia, needle biopsy, fluid aspiration procedures, and other minor surgical procedures and diagnostic tests.

With reference to FIGS. 1-4, the sheet 22 includes a pair of longitudinally extending side edges 24a and 24b, and a pair of laterally extending end edges 26a and 26b connecting the side edges 24a and b. In a preferred embodiment, the sheet 22 has a generally rectangular shape, with the side and end edges being generally parallel. The sheet 22 also has a first surface 28 which contacts the body of a patient after placement of the drape 20, and a second surface 30 which faces away from the patient after placement of the drape.

The drape 20 has first and second spaced lateral fold lines 32 and 34, respectively, which extend between the side edges 24a and b, and which define a laterally extending central panel 36. As shown, the central panel 36 has a fenestration 50 located adjacent a lateral central portion of the central panel. The drape has a third lateral fold line 38 which extends between the side edges 24a and b, and which is located intermediate the central panel 36 and one end edge 26a of the sheet 22. The third fold line 38 defines a laterally extending end panel 40 intermediate the one end edge 26a and the third fold line 38. As shown, the first fold line 32 is located intermediate the second and third fold lines 34 and 38, respectively, and the first and third fold lines 32 and 38 define a laterally extending connecting panel 42 intermediate the fold lines. The drape 20 also has a fourth lateral fold line 44 extending between the side edges 24a and b and defining a first end section 46 extending between the second and fourth fold lines 34 and 44, and a second end section 48 extending between the fourth fold line 44 and the other end edge 26b of the sheet 22. In a preferred embodiment, as shown, the first end section 46 has a width between the second and fourth fold lines 34 and 44 approximately equal to the width of the central panel 36 between the first and second fold lines 32 and 34, such that the fourth fold line 44 is located adjacent the first fold line 32. Also, the width of the connecting panel 42 is less than the width of both the central panel 36 and the end panel 40. As shown, the fenestration 50 in the central panel 36 is located adjacent the second fold line 34 and adjacent a lateral central portion of the central panel 36 intermediate the side edges 24a and b.

The drape 20 is folded in the following manner. The connecting panel 42 is folded over the central panel 36 with the first surface 28 of the connecting panel 42 facing the first surface 28 of the central panel 36. As shown, the end panel 40 is folded against the connecting panel 42 with the second surface 30 of the end panel 40 facing the second surface 30 of the connecting panel 42. The first end section 46 is folded against the central panel 36 with the second surface 30 of the first end section 46 facing the second surface 30 of the central panel 36. Finally, the second end section 48 is folded against the first end section 46 with the first surface 28 of the second end section 48 facing the first surface 28 of the first end section 46.

In this configuration, the other end edge 26b of the drape or sheet is located intermediate the second fold line 34 and the fourth fold line 44 if, as shown, the width of the second end section 48 is less than the width of the first end section 46. Also, both the first end section 46 and second end section 48 are located beneath the central panel 36. As shown, the connecting panel 42 and end panel 40 overlie the central panel 36, such that these panels cover a first end portion 52 of the central panel 36 which extends from the first fold line 32. At the same time, the connecting panel 42 and end panel 40 leave a second end portion 54 of the central panel 36 exposed intermediate the third fold line 38 and the second fold line 34. Also, an end portion 56 of the end panel 40 adjacent the one end edge 26a extends past the first fold line 32 of the sheet, since the width of the end panel 40 is greater than the width of the connecting panel 42. In this configuration, the first surface 28 of the end panel 40 and the first surface 28 of the second end portion 54 of the central panel is exposed on the outside of the drape. As shown, the fenestration 50 is located in the second end portion 54 of the central panel 36, and is exposed in the folded configuration of the drape.

Figure 3:
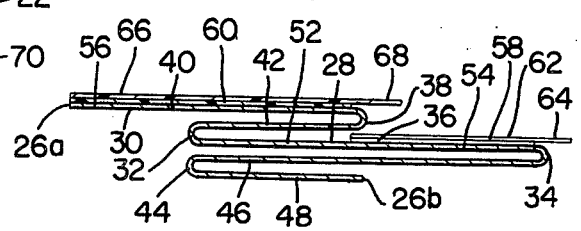
FIG. 3 is a sectional view taken substantially as indicated along the line 3—3 of FIG. 2.
Figure 4:
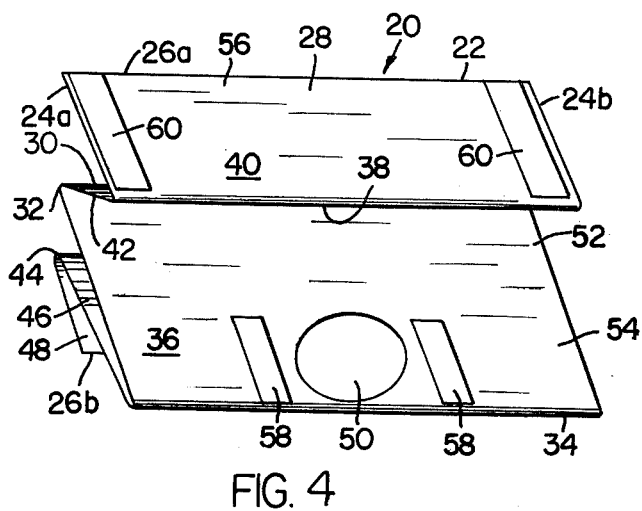
FIG. 4 is a perspective view of the drape of FIG. 2 as further unfolded.

With reference to FIGS. 3 and 4, the drape 20 has a pair of first adhesive zones 58 located on opposed sides of the fenestration 50 and adjacent the fenestration. As shown, the first adhesive zones 58 are located substantially in the second end portion 54 of the central panel 36, and, in the folded configuration of FIGS. 2 and 3, the first adhesive zones 58 extend substantially between the third fold line 38 and the second fold line 34. With reference to FIGS. 3 and 4, the drape has a pair of second adhesive zones 60 located on the end panel 40 and adjacent the side edges 24a and b. In a preferred form, as shown, the second adhesive zones 60 extend substantially between the one end edge 26a and the third fold line 38. The first and second adhesive zones 58 and 60 face outwardly from the first surface 28 of the drape, and may comprise any suitable type of adhesive, such as double-faced adhesive strips. The drape 20 has a first pair of release sheets 62 covering and releasably attached to the first adhesive zones 58. In a preferred form, as shown, the first release sheets 62 have end portions 64 extending past the second fold line 34 to facilitate removal of the first release sheets 62 from the first adhesive zones 58. The drape also has a pair of second release sheets 66 covering and releasably attached to the second adhesive zones 60, and the release sheets 66 may have end portions 68 extending past the third fold line 38, as shown, or, in an alternative form, extending past the one end edge 26a, in order to facilitate removal of the second release sheets 66 from the second adhesive zones 60.

Figure 2:
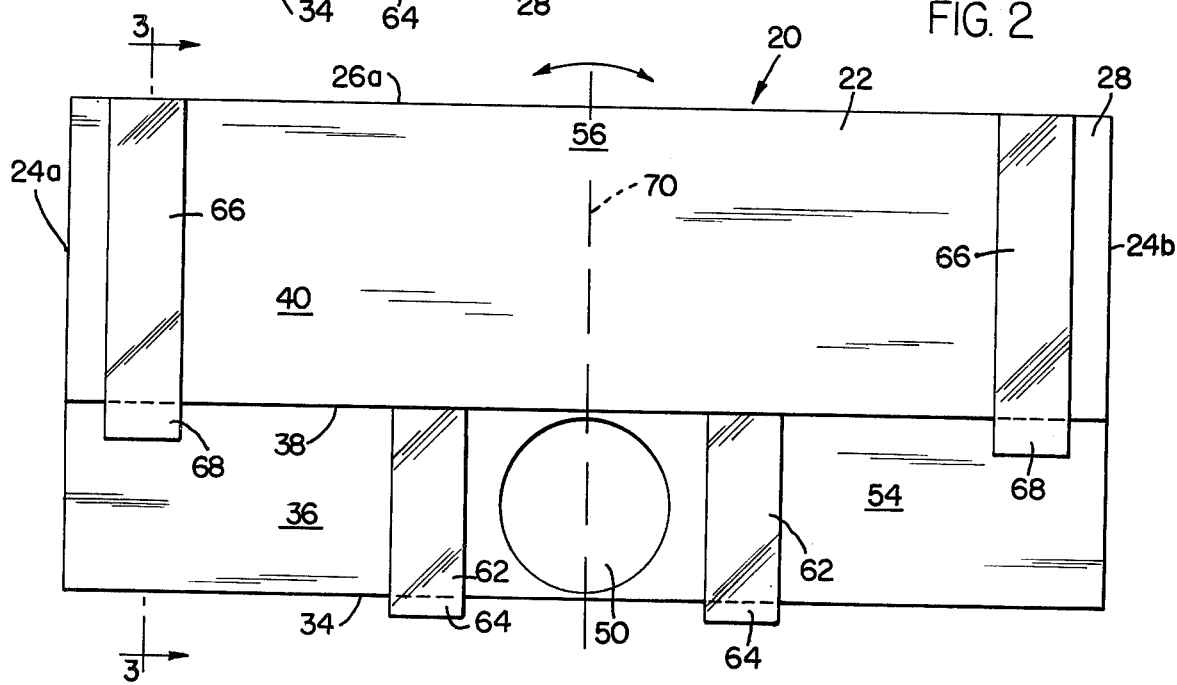
FIG. 2 is a plan view of the drape of FIG. 1 as partially unfolded.

With reference to FIGS. 1-3, the folded drape of FIG. 2 has a longitudinally extending fold line 70 located in a lateral central portion of the drape between the side edges 24a and b, such that the fold line 70 extends between the end edges 26a and b. The drape is folded along the fold line 70 such that the first surface 28 of the end panel 40 and second end portion 54 of the central panel 36 is exposed on the outside of the drape, as shown in FIG. 1.

During use, with reference to FIG. 1, the drape 20 is unfolded about the longitudinally extending fold line 70 into the configuration as shown in FIG. 2. In this configuration, the release sheets 62 and 66 are exposed on the outside of the drape 20 to permit removal of the release sheets and expose the underlying adhesive zones. If desired, both the first release sheets 62 and the second release sheets 66 may be removed to expose the first and second adhesive zones for use in placement of the drape on a larger-sized patient, such as an adult. Alternatively, the first release sheets 62 may be removed to expose only the first adhesive zones 58 for placement of the drape on a smaller-sized patient, such as an infant. If desired, the second release sheets 66 may be removed to expose the second adhesive zones 60 while leaving the first release sheets 62 in place on the first adhesive zones 58. As previously indicated, the end portions 64 of the first release sheets 62 and the end portions 68 of the second release sheets 66 facilitate removal of the release sheets from the respective adhesive zones and minimize the possibility of contamination to the drape during removal of the release sheets. The drape of the present invention is illustrated in FIG. 4 with all of the release sheets removed from the drape, such that both the first adhesive zones 58 and the second adhesive zones 60 are exposed on the outside of the drape.

Once the release sheets have been removed and the desired adhesive zones have been exposed, the drape may be grasped by the end panel 40 adjacent the second adhesive zones 60, and the end panel 40 may be lifted in order to laterally unfold the drape, as shown in FIGS. 4 and 5. Next, the second adhesive zones 60, if exposed, may be attached to an upper portion of the patient's body, and the first adhesive zones 58 may be attached to the patient's body with the fenestration 50 located at the desired position on the patient. Alternatively, for a patient having a smaller body size, such as an infant, the first adhesive zones 58 may be utilized to secure the drape on the patient adjacent the fenestration 50, while the second release sheets 66 remain on the second adhesive zones 60, such that the upper portion of the drape 20 may be folded over the infant. Thus, the drape of the present invention may be properly positioned and retained in place on a patient irrespective of body size. Further, as previously discussed, the drape may be readily unfolded and the selected adhesive may be readily exposed for convenient placement of the sterile drape without contamination.

The foregoing detailed description is given for clearness of understanding only, and no unnecessary limitations should be understood therefrom, as modifications will be obvious to those skilled in the art.

We claim:

1. A folded drape, comprising:

a sterile sheet of flexible material including,
a pair of side edges extending longitudinally along the sheet,
a pair of laterally extending end edges connecting said side edges,
a first surface for contacting the body of a patient after placement of the drape,
a second surface facing away from the patient after placement of the drape,
first and second spaced lateral fold lines extending between said side edges and defining a laterally extending central panel having a fenestration located adjacent a lateral central portion thereof,
a third lateral fold line extending between said side edges and located intermediate the central panel and one of said end edges, said third fold line defining a laterally extending end panel intermediate said one end edge and said third fold line, said first fold line being located intermediate said second and third fold lines,
at least one laterally extending connecting panel intermediate said first and third fold lines, said connecting panel being folded into a configuration overlying the first surface of a first end portion of the central panel, said first end portion being covered between the first and third fold lines, said third fold line being spaced from the second fold line and the first surface of a second end portion of the central panel being exposed intermediate said second and third fold lines, said fenestration being located in said second end portion, and said first surface of the end panel being exposed in the folded configuration, and at least one end section extending from the second fold line and folded beneath the central panel;
a pair of first adhesive zones located on opposed sides of and adjacent the fenestration in said second end portion of the central panel, said first adhesive zones facing outwardly from said first surface;
a pair of first release sheets covering and releasably attached to said first adhesive zones;
a pair of second adhesive zones on said end panel adjacent opposed side edges of the sheet, said second adhesive zone facing outwardly from said first surface; and
a pair of second release sheets covering and releasably attached to said second adhesive zones.

2. The drape of claim 1 wherein said first adhesive zones extend substantially between said second and third fold lines of the folded sheet.

3. The drape of claim 1 wherein said first release sheets include an end portion extending past said second fold line.

4. The drape of claim 1 wherein said second adhesive zones extend substantially between said one end edge and said third fold line.

5. The drape of claim 1 wherein said second release sheets include an end portion extending past said third fold line.

6. The drape of claim 1 wherein said sheet includes one connecting panel extending between the first and third fold lines, said second surface of the end panel is folded against the second surface of the connecting panel, and said first surface of the connecting panel is folded against the first surface of the central panel.

7. The drape of claim 1 wherein said end panel includes an end portion adjacent said one end edge extending past said first fold line.

8. The drape of claim 1 including a longitudinal fold line extending between said end edges, said longitudinal fold line defining side panels folded together with the first surface of said end panel being exposed.

9. The drape of claim 1 wherein said sheet includes a fourth lateral fold line extending between said side edges, said fourth fold line defining a first end section intermediate the second and fourth fold lines, and a second end section intermediate the fourth fold line and the other end edge of said sheet, said first end section being folded against the central panel with the second surface of the first end section facing the second surface of the central panel and with said fourth fold line located adjacent said first fold line, said second end section being folded against the first end section with the first surface of the second end section facing the first surface of the first end section.

10. The drape of claim 9 wherein said other end edge is located intermediate said second and fourth fold lines.

* * * * *